US00PP12985P2

(12) United States Plant Patent
Mukundan et al.

(10) Patent No.: US PP12,985 P2
(45) Date of Patent: Sep. 17, 2002

(54) AGLAONEMA PLANT NAMED 'SILVER RIBBONS'

(76) Inventors: Parthasarathy Mukundan, "Srinivasa", 237/46, Fifth Main Road, Chamrajpet, Bangalore 560018 (IN); Gopalaswamy Parthasarathy, "Srinivasa", 237/46, Fifth Main Road, Chamrajpet, Bangalore 560018 (IN)

( * ) Notice: Subject to any disclaimer, the term of this patent is extended or adjusted under 35 U.S.C. 154(b) by 39 days.

(21) Appl. No.: 09/812,117

(22) Filed: Mar. 19, 2001

(51) Int. Cl.[7] ..... A01H 5/00

(52) U.S. Cl. ..... Plt./376

(58) Field of Search ..... Plt./376, 373

*Primary Examiner*—Bruce R. Campell
*Assistant Examiner*—June Hwu
(74) *Attorney, Agent, or Firm*—C. A. Whealy

(57) ABSTRACT

A distinct cultivar of Aglaonema plant named 'Silver Ribbons', characterized by its compact, upright and outwardly arching growth habit; relatively rapid growth rate and fast rooting; freely clumping habit, full and dense plants; twisted, long, narrowly lanceolate, undulate, and sharply acuminate leaves with random green spots and blotches on a silver green background and green leaf margins; and good postproduction longevity.

2 Drawing Sheets

BACKGROUND OF THE INVENTION

The present Invention relates to a new and distinct cultivar of Aglaonema plant, botanically known as *Aglaonema commutatum* var. *picturatum* and hereinafter referred to by the name 'Silver Ribbons'.

The new Aglaonema is the result of a planned breeding program conducted by the Inventors in Chamrajpet, Bangalore, India. The objective of the breeding program is to create new Aglaonema cultivars with compact plant habit, unique leaf variegation patterns, interesting leaf shapes, and resistance to pathogens.

The new Aglaonema originated from a cross made by the Inventors of the *Aglaonema commutatum* var. *picturatum* cultivar Treubii, as the female, or seed, parent with the *Aglaonema commutatum* var. *picturatum* cultivar Silver III, as the male, or pollen, parent. The new Aglaonema was discovered and selected by the Inventors in 1989 as a single plant within the progeny of the stated cross in a controlled environment in Chamrajpet, Bangalore, India. The new Aglaonema was selected on the basis of its compact habit and unique leaf shape and variegation pattern.

Asexual propagation of the new cultivar by cuttings or by divisions in Chamrajpet, Bangalore, India, has shown that the unique features of this new Aglaonema are stable and reproduced true to type in successive generations.

SUMMARY OF THE INVENTION

The following traits have been repeatedly observed and are determined to be the unique characteristics of 'Silver Ribbons'. These characteristics in combination distinguish 'Silver Ribbons' as a new and distinct cultivar:

1. Compact, upright and outwardly arching growth habit.
2. Relatively rapid growth rate and fast rooting.
3. Freely clumping habit, full and dense plants.
4. Twisted, long, narrowly lanceolate, undulate, and sharply acuminate leaves with random green spots and blotches on a silver green background and green leaf margins.
5. Good postproduction longevity.

In side-by-side comparisons conducted by the Inventors in Chamrajpet, Bangalore, India, plants of the new Aglaonema differed from plants of the female parent, the *Aglaonema commutatum* var. *picturatum* cultivar Treubii, in the following characteristics:

1. Plants of the new Aglaonema are freely-clumping and produce more offshoots per plant than plants of the cultivar Treubii.
2. Plants of the new Aglaonema have more leaves and are more dense than plants of the cultivar Treubii.
3. Plants of the new Aglaonema grow faster and are more resistant to pathogens than plants of the cultivar Treubii.
4. Leaves of plants of the new Aglaonema are almost twice as long as leaves of plants of the cultivar Treubii.
5. Leaves of plants of the new Aglaonema and the cultivar Treubii differ in leaf variegation pattern and color.
6. Leaves of plants of the new Aglaonema are twisted and undulate whereas leaves of plants of the cultivar Treubii are flat.

In side-by-side comparisons conducted by the Inventors in Chamrajpet, Bangalore, India, plants of the new Aglaonema differed from plants of the male parent, the *Aglaonema commutatum* var. *picturatum* cultivar Silver III, in the following characteristics:

1. Plants of the new Aglaonema are freely-clumping and produce more offshoots per plant than plants of the cultivar Silver III.
2. Plants of the new Aglaonema have more leaves and are more dense than plants of the cultivar Silver III.
3. Plants of the new Aglaonema grow faster and are more resistant to pathogens than plants of the cultivar Silver III.
4. Leaves of plants of the new Aglaonema are narrower and almost twice as long as leaves of plants of the cultivar Silver III.
5. Leaves of plants of the new Aglaonema and the cultivar Silver III differ in leaf variegation pattern and color.
6. Leaves of plants of the new Aglaonema are twisted and undulate whereas leaves of plants of the cultivar Silver III are flat.

In side-by-side comparisons conducted by the Inventors in Chamrajpet, Bangalore, India, plants of the new Aglaonema differed from plants of the Aglaonema cultivar Black Lance, disclosed in U.S. Plant Pat. No. 10,280, in the following characteristics:

1. Plants of the new Aglaonema are more compact than plants of the cultivar Black Lance.

2. Plants of the new Aglaonema are more freely-clumping and produce more offshoots per plant than plants of the cultivar Black Lance.

3. Plants of the new Aglaonema have more leaves and are more dense than plants of the cultivar Black Lance.

4. Leaves of plants of the new Aglaonema have darker green petioles than plants of the cultivar Black Lance.

5. Leaves of plants of the new Aglaonema and the cultivar Black Lance differ in leaf variegation pattern and color.

6. Leaves of plants of the new Aglaonema are twisted and undulate whereas leaves of plants of the cultivar Black Lance are flat.

In side-by-side comparisons conducted by the Inventors in Chamrajpet, Bangalore, India, plants of the new Aglaonema differed from the Aglaonema cultivar Rhapsody in Green, disclosed in U.S. Plant Pat. No. 8,975, in the following characteristics:

1. Plants of the new Aglaonema are more compact than plants of the cultivar Rhapsody in Green.

2. Plants of the new Aglaonema are more freely-clumping and produce more offshoots per plant than plants of the cultivar Rhapsody in Green.

3. Plants of the new Aglaonema have more leaves and are more dense than plants of the cultivar Rhapsody in Green.

4. Leaves of plants of the new Aglaonema are narrower than leaves of plants of the cultivar Rhapsody in Green.

5. Leaves of plants of the new Aglaonema and the cultivar Rahpsody in Green differ in leaf variegation pattern and color.

6. Leaves of plants of the new Aglaonema are twisted and undulate whereas leaves of plants of the cultivar Rhapsody in Green are flat.

BRIEF DESCRIPTION OF THE PHOTOGRAPHS

The accompanying colored photographs illustrate the overall appearance of the new Aglaonema, showing the colors as true as it is reasonably possible to obtain in colored reproductions of this type. Colors in the photographs may differ slightly from the color values cited in the detailed botanical description which accurately describe the colors of the new Aglaonema.

The photograph on the first sheet comprises a side perspective view of a typical plant of 'Silver Ribbons'.

The photograph on the second sheet comprise is a close-up view of a typical bare-rooted plant of the new Aglaonema. Plants used in the photographs were similar in age to those used in the following detailed botanical description.

DETAILED BOTANICAL DESCRIPTION

The cultivar Silver Ribbons has not been observed under all possible environmental conditions. The phenotype may vary somewhat with variations in environment such as temperature, light intensity and/or fertilizer rate, without, however, any variance in genotype.

In the following observations, measurements and values describe plants of the new Aglaonema grown in 24-cm containers, in Miami, Fla., in a polypropylene-covered shadehouse and finished during the summer. Plants used for this description were grown in the containers for about eight months. Color references are made to The Royal Horticultural Society Colour Chart except where general terms of ordinary dictionary significance are used.

Botanical classification: *Aglaonema commutatum* var. *picturatum* cultivar Silver Ribbons.

Parentage:

*Female, or seed, parent.*—*Aglaonema commutatum* var. *picturatum* cultivar Treubii, not patented.

*Male, or pollen, parent.*—*Aglaonema commutatum* var. *picturatum* cultivar Silver III, not patented.

Propagation:

*Type.*—By cuttings.

*Time to initiate roots.*—Summer: About 14 days at 27 to 35° C. Winter: About 20 days at 20 to 25° C.

*Time to produce a rooted plant.*—Summer: About 21 days at 27 to 35° C. Winter: About 30 to 35 days at 20 to 25° C.

*Root description.*—Thick, fibrous and fleshy.

Plant description:

*Appearance.*—Erect when young, becoming more outwardly arching and spreading as leaves develop; inverted triangle, symmetrical. Freely clumping habit give plants a very fully and dense appearance. Relatively compact, appropriate for 14 to 24-cm containers.

*Plant height.*—About 30 cm.

*Plant width.*—About 62 cm.

*Growth rate/vigor.*—Vigorous, rapid growth rate.

*Stem color.*—Darker than 144A.

*Branching habit.*—Freely clumping habit; plants typically produce about 20 offshoots per plant; full and dense plants.

*Foliage description.*—Length: About 22.5 cm. Width: About 5 cm. Shape: Narrowly lanceolate. Apex: Sharply acuminate. Base: Obtuse. Margin: Entire, undulating. Orientation: Initially upright to outwardly arching. Surface: Rugose, undulating, twisted. Texture: Smooth, glabrous; thick and leathery. Midrib: Prominent on the lower surface. Primary veins: Recessed on upper surface and prominent on lower surface. Color: Young leaves, upper surface: Background, silvery green, close to 147C, shiny; random spots and margin, dark green, 146A. Young leaves, lower surface: 146B, shiny. Fully expanded leaves, upper surface: Background, silvery green, close to 148B to 148C, shiny; random spots and margin, dark green, 147A and 147B; venation, 147A. Fully expanded leaves, lower surface: More green than 147B, shiny; venation, 147B. Petiole: Length: About 20 cm. Diameter, at leaf base: About 3.5 cm. Diameter, base: About 7.5 cm. Wing length: About 12 cm. Wing width: About 4 mm. Color: Towards apex, 146A, becoming lighter green to 146D towards base.

Inflorescence description: Inflorescence development has not been observed on plants of the new Aglaonema grown under shadehouse production conditions.

Disease resistance: Plants of the new Aglaonema have been shown to be resistant to pathogens common to Aglaonema.

It is claimed:

1. A new and distinct cultivar of Aglaonema plant named 'Silver Ribbons', as illustrated and described.

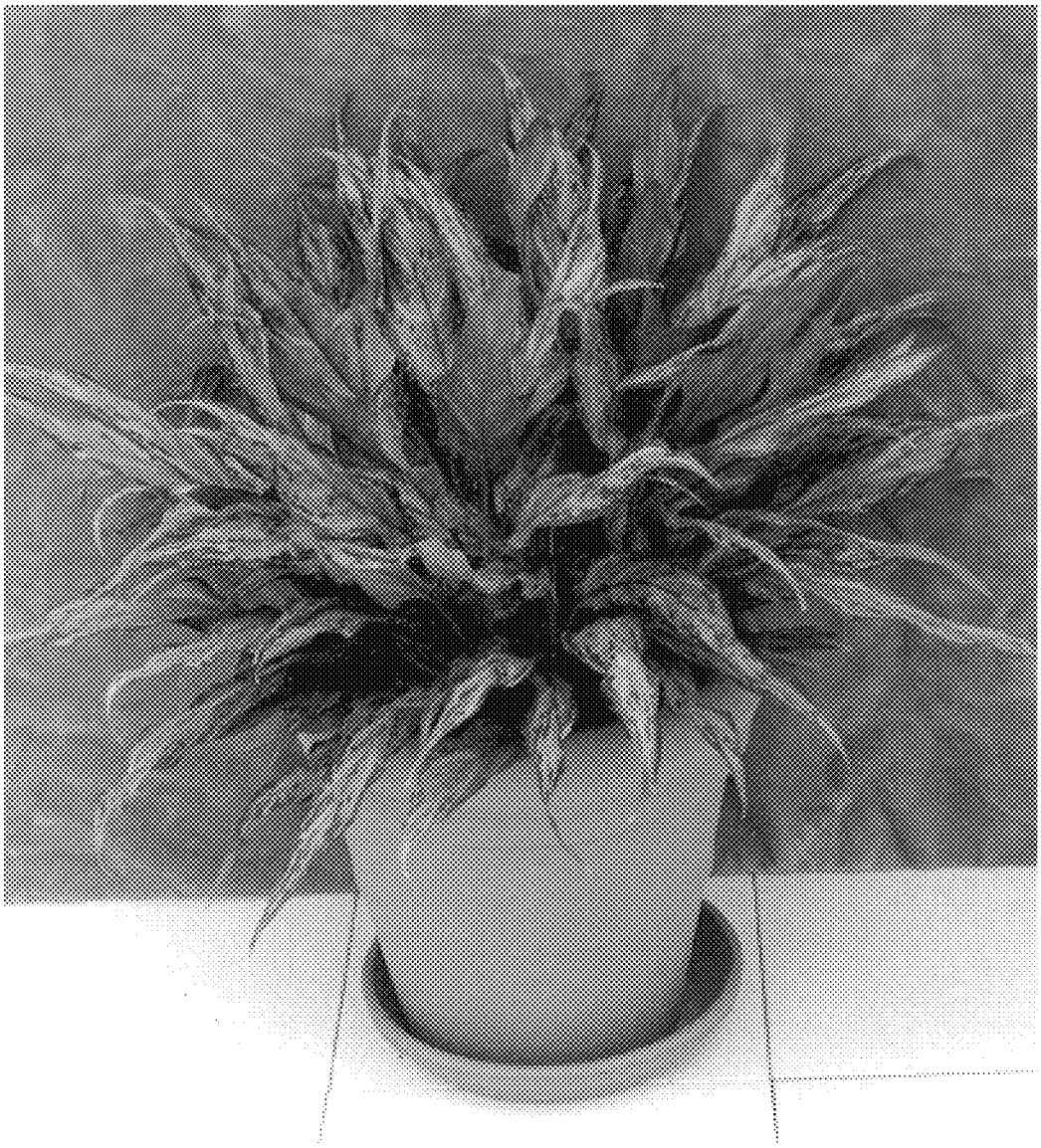

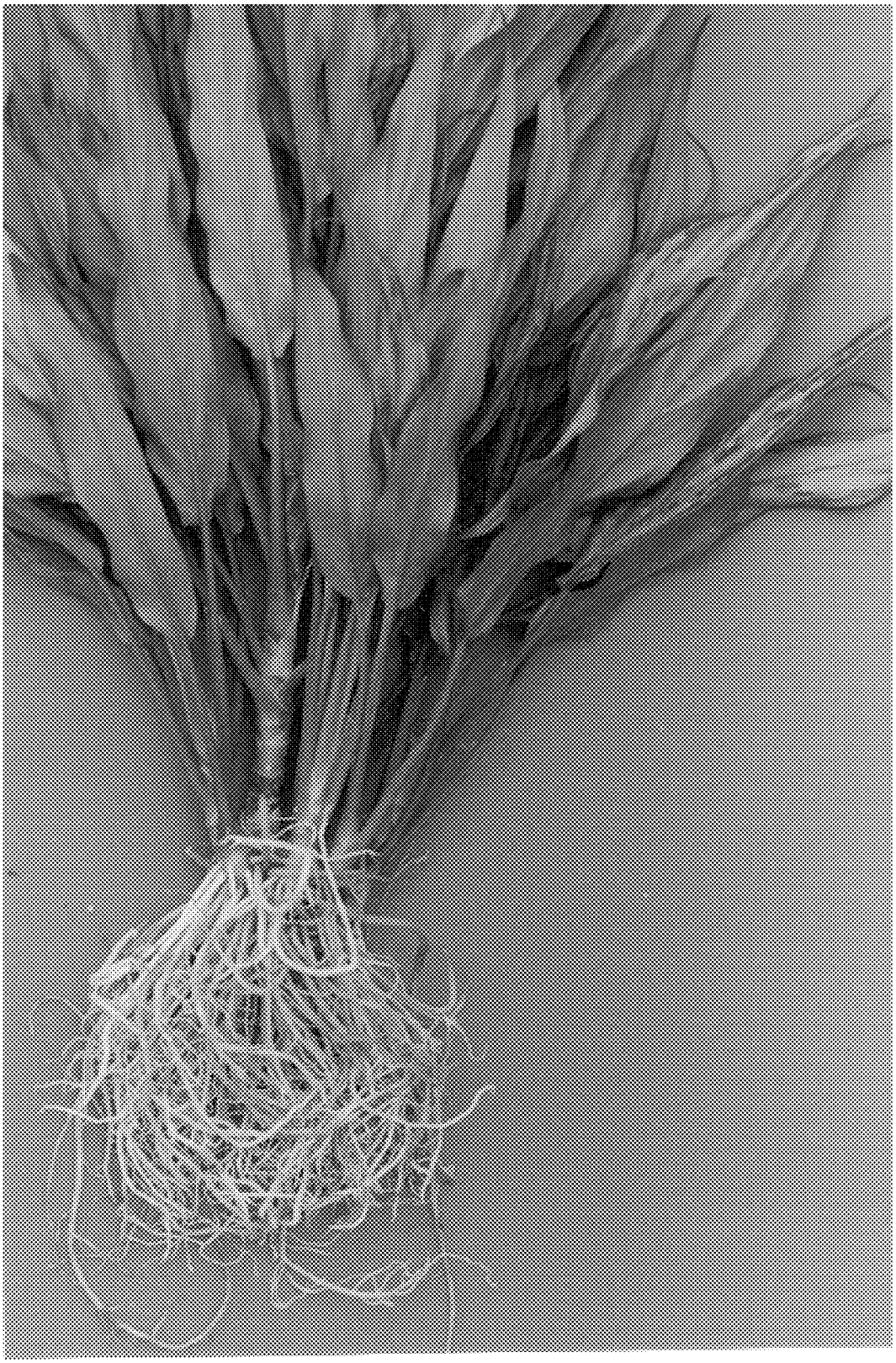

* * * * *